(12) United States Patent
Hogrel et al.

(10) Patent No.: US 9,289,171 B2
(45) Date of Patent: Mar. 22, 2016

(54) DEVICE FOR MEASURING THE PINCH FORCE BETWEEN A PERSON'S THUMB AND INDEX FINGER

(71) Applicant: ASSOCIATION INSTITUT DE MYOLOGIE, Paris (FR)

(72) Inventors: Jean-Yves Hogrel, Montrouge (FR); Amelie Moraux, Paris (FR)

(73) Assignee: ASSOCIATION INSTITUT DE MYOLOGIE, Paris (FR)

( * ) Notice: Subject to any disclaimer, the term of this patent is extended or adjusted under 35 U.S.C. 154(b) by 0 days.

(21) Appl. No.: 14/427,981

(22) PCT Filed: Sep. 13, 2013

(86) PCT No.: PCT/FR2013/052106
§ 371 (c)(1),
(2) Date: Mar. 12, 2015

(87) PCT Pub. No.: WO2014/041315
PCT Pub. Date: Mar. 20, 2014

(65) Prior Publication Data
US 2015/0216467 A1  Aug. 6, 2015

(30) Foreign Application Priority Data

Sep. 14, 2012 (FR) ..................... 12 58673

(51) Int. Cl.
*A61B 5/22* (2006.01)
*A61B 5/00* (2006.01)

(52) U.S. Cl.
CPC .............. *A61B 5/225* (2013.01); *A61B 5/0002* (2013.01); *A61B 2560/0223* (2013.01); *A61B 2562/0261* (2013.01)

(58) Field of Classification Search
CPC .................................. A61B 1/24; A61B 5/22

USPC ......................................... 73/379.02, 379.01
See application file for complete search history.

(56) References Cited

U.S. PATENT DOCUMENTS

| 4,467,815 A | 8/1984 | O'Brien et al. |
| 5,125,270 A | 6/1992 | Kovacevic |
| 5,413,611 A * | 5/1995 | Haslam, II .............. A61F 2/583 623/24 |
| 2004/0144156 A1 | 7/2004 | Becker et al. |
| 2004/0177686 A1* | 9/2004 | Johansson .............. A61B 5/225 73/379.01 |
| 2012/0094260 A1 | 4/2012 | Akins et al. |

FOREIGN PATENT DOCUMENTS

| DE | 3518489 A1 | 12/1986 |
| WO | 2011044520 A1 | 4/2011 |

OTHER PUBLICATIONS

English Translation of International Search Report of PCT/FR2013/052106 dated Dec. 18, 2013.

* cited by examiner

*Primary Examiner* — Jewel V Thompson
(74) *Attorney, Agent, or Firm* — Amster, Rothstein & Ebenstein LLP

(57) ABSTRACT

The invention relates to a device for measuring the pinch force between a person's thumb and index finger, comprising: first and second parallel blades, said blades being disposed at a distance from one another and embedded at a first longitudinal end thereof; a sensor for measuring the pinch force exerted between the two blades at the second longitudinal end thereof, perpendicularly to the respective main planes thereof; a means for displaying the pinch force; and a means for storing and/or processing the pinch force. According to the invention, the first blade forms part of a rigid parallelepiped frame and the second blade is disposed in the space inside the parallelogram.

11 Claims, 2 Drawing Sheets

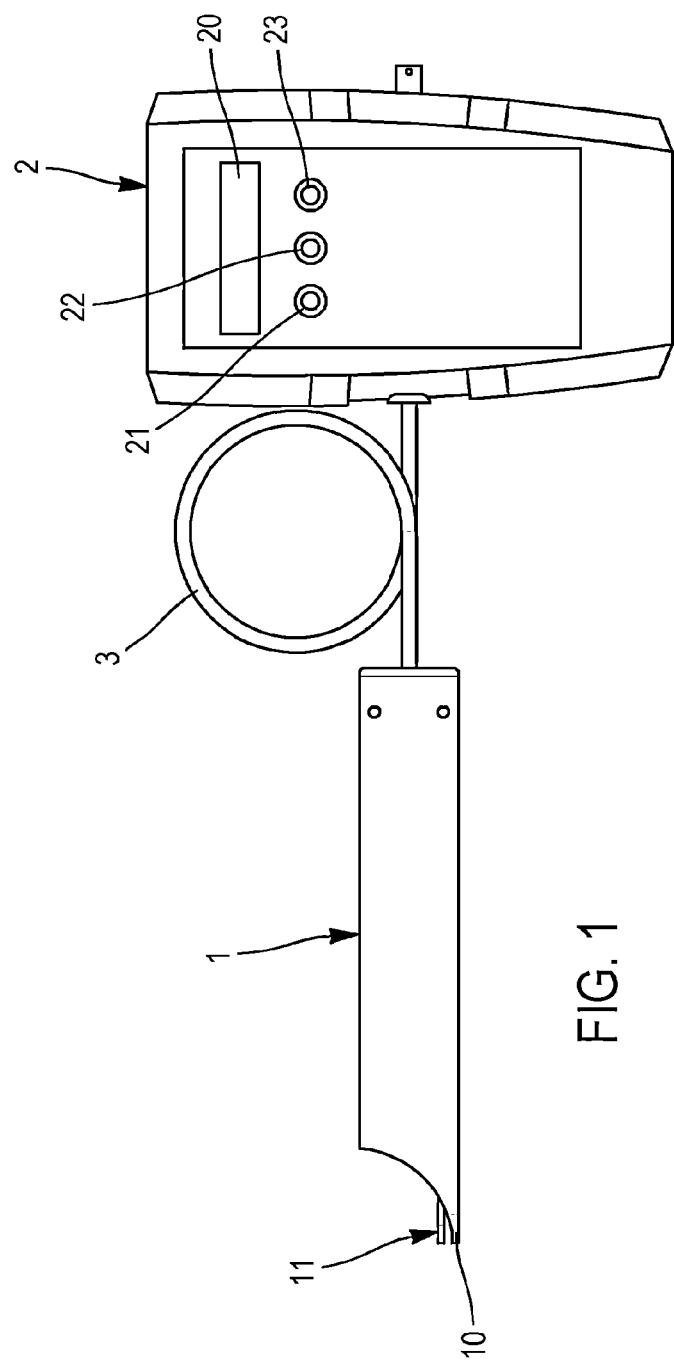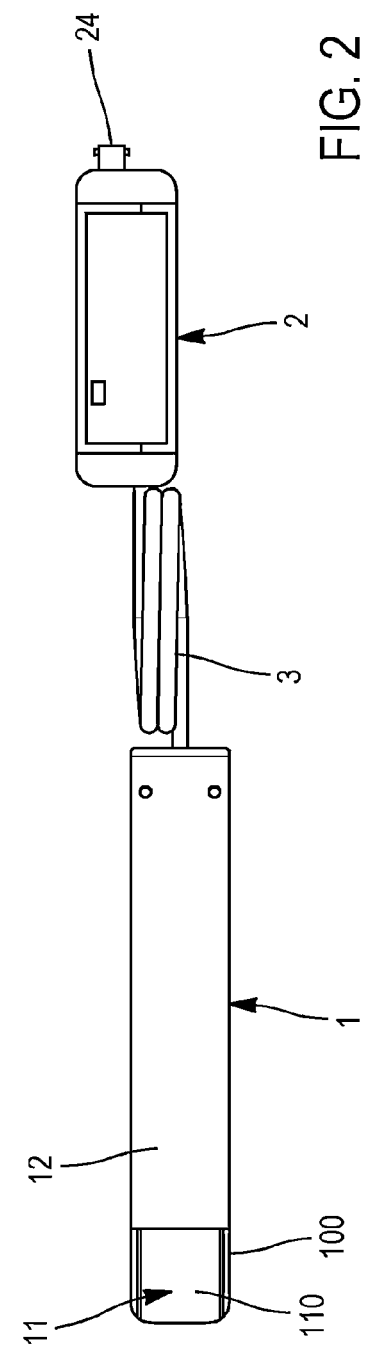

DEVICE FOR MEASURING THE PINCH FORCE BETWEEN A PERSON'S THUMB AND INDEX FINGER

TECHNICAL FIELD OF THE INVENTION

Figure 3:
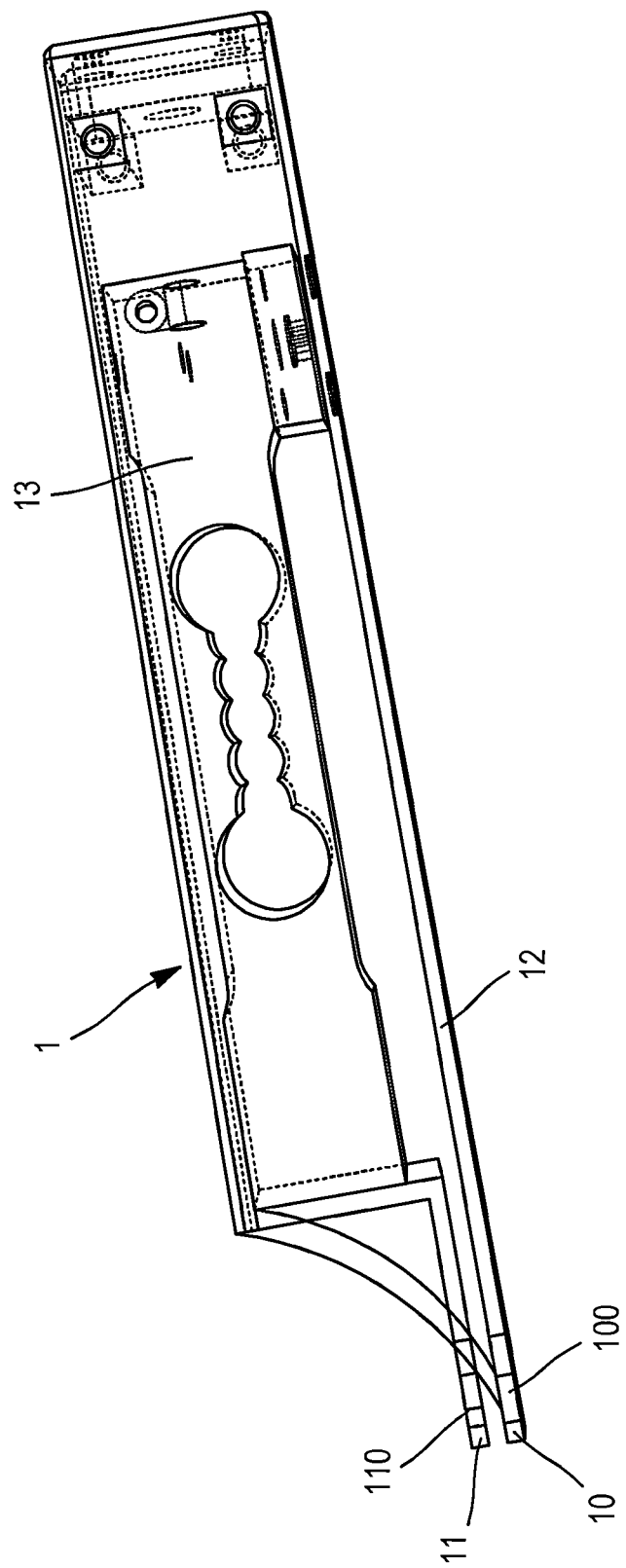

The invention relates to the field of measuring the manual pinch effort (or force) between a person's thumb and index finger. It is therefore a question of measuring, displaying, processing this force, in particular relative to disabled persons who can exert only very weak pinch forces.

PRIOR ART

Devices are already known for measuring the pinch but they are often dedicated to people in good health in such a way that very weak forces cannot be measured and processed with effectiveness and reliability.

For example document U.S. Pat. No. 4,674,330 which discloses a device that comprises two parallel branches embedded at one of the ends on a part in the shape of a bracket and of which the two free ends are subjected to a pinch force from the user who therefore exerts this force between his thumb and index finger on free ends of the device. Strain gauges are arranged in one of the branches of this device in such a way that the force measured can be applied at all points of the ends. In addition this device has the particularity of being able to modify the distance between the branches, in order to adapt to a second type of measurement namely the palm grasping force of a person. This device therefore has the characteristic of a dual functionality. The precision expected and required for measuring the pinch of a highly disabled person is however not obtained with such a device.

US patent 2012/0137772 also discloses a device with dual functionality namely the measurement of a palm force and the measurement of a force between two fingers. The operating principle of this device is removed from that presented hereinabove. The structure associated with this dual functionality is also removed from that of this invention; in particular no pressure chamber is required although this device of prior art is based on such a use.

As technological background a system is known for calibrating the device for measuring the pinch force, such as in U.S. Pat. No. 6,868,710 B1. This here entails calibrating a device for measuring known per se and shown for example in FIG. 2 of this document. The device for measuring is of the hydraulic, not mechanical, type.

Unfortunately the known devices do not allow for measurements that are both precise and for low force values.

DISCLOSURE OF THE INVENTION

The invention aims to overcome the disadvantages of prior art with a view in particular to study the isometric performance of muscles in highly disabled persons as well as persons in good health, children and adults. A reliability and a precision for the measurements are operated according to the invention, in a manner that is not yet obtained to date.

To do this according to a first aspect of the invention a device for measuring the pinch force between a person's thumb and index finger is proposed, comprising first and second parallel blades and at a distance from one another, maintained integral with a first longitudinal end, a sensor for measuring the pinch force exerted between the two blades on their second longitudinal ends perpendicularly to the respective main planes thereof, a means for displaying said pinch force, a means for storing and/or processing said pinch force.

According to a characteristic of the invention, said first blade forms part of a rigid frame and said second blade is arranged in the space inside said rigid frame. As such, the two blades are connected by the sensor according to a particular configuration.

Preferably, the rigid frame has the outside shape of a parallelogram. In the rest of this text the expression "rigid frame" can be assimilated to "first part of the device" in that it includes the elements that comprise said first part.

This characteristic arrangement of the measuring device, in addition to the advantages already mentioned hereinabove, makes it possible to overcome problems linked to the way in which the subject and/or the evaluator hold the device. It is then ensured that, during operation, the device is always held adequately because the exposed surfaces, namely the ends of the blades which constitute the functional contact surfaces, are the only contact surfaces possible by the subject.

Advantageously, said rigid frame has a cylindrical, parallelepiped or substantially parallelepiped exterior shape.

The sensor for measuring said force is a sensor, more preferably with a strain gauge, integrated into the space inside said rigid frame and arranged in such a way as to engage functionally with the first and second blade. Of course, other sensors known to those skilled in the art can be used without leaving the scope of the invention. For example and in a non-restricted manner, a piezoelectric sensor or an electromagnetic compensation sensor can be used.

For example, the sensor for measuring said force is a strain gauged sensor, like those used in precision balances, fixed in suspension in the inside space of said rigid frame, and engaging functionally with the first and second blades.

As such the rigid frame constitutes a protection for the sensor itself as well as for the other sensitive components of the device. The disturbances and/or degradations of the sensitive parts of the device are therefore advantageously reduced. The sensor itself, of great sensitivity, is protected which guarantees perfect reliability and quality of the measurements. This constitutes a considerable advantage in particular when very weak forces must be measured.

Moreover, the device according to the invention comprises a means for clearing the force measured, regardless of the spatial position of the device. This aspect is interesting in order to overcome the effects of gravity to which the sensor is sensitive and which can distort the measurement when the latter is small.

Advantageously, the device for measuring according to the invention can comprise a safety means intended to prevent untimely contact between the second longitudinal ends of said blades, when the force exerted is greater than or equal to a given threshold S1. The safety means can consist of an alarm (visual, audible or other) or of a mechanical element.

Interestingly the device according to the invention further comprises a means for calibrating said force exerted. This means can have various forms without leaving the scope of the invention.

Advantageously the device for measuring further comprises a means for the wireless transmission of the signal relating to said pinch force recorded by said force sensor.

Without leaving the scope of the invention, the device for measuring further comprises a means of remotely communicating with a device for processing and/or storing data of the computer type.

Particularly advantageously, the device according to the invention further comprises a means intended for the remote triggering of the acquisition of the signal concerning said pinch force. Of course this option is interesting in many situations in particular when the measuring environment is difficult, poorly suited.

The device according to the invention can operate thanks to an autonomous power source of the battery type and/or from the mains.

According to a preferred embodiment of the invention, said means for displaying, and clearing are part of an independent case of the rigid frame for acquiring data.

Other characteristics and advantages of the invention shall appear when reading the following description, in reference to the annexed figures, which show:

FIG. 1, a side view of a first embodiment of the invention;
FIG. 2, a top view of the device according to the invention; and
FIG. 3, a longitudinal cross-section of a portion of the device according to the invention.

For increased clarity, identical or similar elements are marked with identical reference signs in all of the figures.

DETAILED DESCRIPTION OF AN EMBODIMENT

FIG. 1 shows for the purposes of information the main elements that comprise the invention. A first part 1 for taking measurements and a second part 2 for processing, displaying and transmitting measurements are shown in particular. The two parts are preferably connected by a connection cord 3.

The first part comprises in particular a first blade 10 as well as a second blade 11; the two blades are parallel to one another, at a given distance from one another, for example about seven millimeters. The first 10 and the second 11 blades can be considered as embedded on one first longitudinal end and they engage with a force sensor 13 in such a way that a pinch on the second longitudinal and distal ends of said blades, exerted perpendicularly to the respective main planes thereof, is directly passed on to said force sensor 13.

The second part or second module 2 can comprise a device for displaying 20 of a type known per se, for example with a digital display; it can display one or more parameters simultaneously and/or in an alternating manner, as explained hereinafter. At least one first contactor 21 can furthermore be provided in order to modify the state (stopped or operating) of the device; at least one second contactor-switch 22 can be arranged on second module 2 in order for example to trigger a function for clearing the measurements.

In addition a third contactor 23 can be provided in order to remotely trigger the acquisition of the signal given by the force sensor 13. This functionality is obtained by any means known in itself by those skilled in the art. For example, it entails a character in a string of information sent via Wi-Fi. Of course this functionality is interesting as it is possible as such to take measurements in a first location, and to transfer these measurements in real time (or possibly deferred) for example to a computer making it possible to record and to process, in real time or not, the measurement signals acquired by the force sensor 13. A Wi-Fi signal is mentioned here, which has to be synchronised with the other transmission signals.

Without leaving the scope of the invention, a BNC socket 24 can be provided for the wired transmission of the data of the force sensor 13 to an acquisition system. FIG. 2 supplements FIG. 1 with regards to the outside arrangement of an embodiment of the invention.

FIG. 3 diagrammatically shows the functional assembly of the first part 1, here with an exterior parallelepiped shape since it is delimited by a rigid frame 12 of parallelepiped shape. The force sensor 13 is integrated therein in such a way that a first surface is fixed and in contact with the first blade 10 while a second surface is fixed and in contact with the second blade 11. The first blade 10 is advantageously constituted by a face of the rigid frame 12 of which a portion 100 is intended to be in contact with a finger of the user; the second blade 11 comprises a portion fixed and in contact with the second functional surface of the sensor 13 which is here parallel to the first surface. The second blade 11 comprises an end surface 110 intended to be in contact with one of the fingers of the user. This second blade is therefore partially integrated into the frame 12 and partially exposed on its functional end surface 110.

The contact surfaces 100 and 110 are the distal surfaces respectively of the first 10 and second 11 blades. For the purposes of information said functional contact surfaces have a length of about 25 mm and a width that is close or greater.

Advantageously the characteristics of the sensor 13, for example a sensor of the AQ10 type marketed by the Scaime company, allow the system to achieve a precision of 10 grams and a resolution de 1 gram. Furthermore, this results in a stability in the measurements over time. Arranged as such, the sensor 13 allows for a reliable transmission of the force values, preferably in real time; the values can be transmitted deferred without leaving the scope of the invention. In addition, these values can be displayed in real time or deferred on the second module 2 or of course on any other support such as for example the screen of a computer (not shown). According to the configuration of the second part 2, the maximum value of the force recorded, over a given period, can also be displayed. This value can also be cleared. Of course, other statistical, evaluative and other processing can be carried out on the signal given by the sensor 13, without leaving the scope of the invention. The results of this processing can be used during the measurements, in order for example to optimise the measurements. These results can be processed later in particular for the purposes of divers and varied analyses such as the time for upscaling the force, the stability of the force during maximum or sustained sub-maximum forces, stress during the dynamic repetition of maximum efforts, etc.

The preferred operating procedure is as follows: the first part 1 of the device according to the invention is held by the evaluator who must pinch the functional surfaces 100 and 110 between the second phalanx of his index finger and the flesh of his thumb. The wrist is not flexed and the thumb is tight; the first part 1 of the device is placed in the alignment of the forearm of the user which is comfortably placed on a flat surface. The second part 2 of the device can be placed in the vicinity of or at a distance from the first part 1.

The invention claimed is:

1. Device for measuring the pinch force between a person's thumb and index finger, comprising first and second parallel blades and at a distance from one another, maintained integral with a first longitudinal end, a sensor for measuring the pinch force exerted between the two blades on their second longitudinal ends perpendicularly to the respective main planes thereof, a means for displaying said pinch force, a means for storing and/or processing said pinch force, wherein said first blade forms part of a rigid frame and in that said second blade is arranged in the inside space of said rigid frame.

2. Device according to claim 1, wherein said rigid frame has a cylindrical, parallelepiped or substantially parallelepiped exterior shape.

3. Device according to claim 1, wherein the sensor for measuring said force is a sensor, more preferably with a strain gauge, integrated into the inside space of said rigid frame and arranged in such a way as to engage functionally with the first and second blades.

4. Device according to claim 1, further comprising a means for clearing the force measured, regardless of the spatial position of the device.

5. Device according to claim 1, further comprising a safety means intended to prevent untimely contact between the second longitudinal ends of said blades, when the force exerted is greater than or equal to a given threshold S1.

6. Device according to claim 1, further comprising a means for calibrating said force exerted.

7. Device according to claim 1, further comprising a means for the wireless transmission of the signal relating to said pinch force recorded by said force sensor.

8. Device according to claim 1, further comprising a means intended for the remote triggering of the acquisition of the signal concerning said pinch force.

9. Device according to claim 1, further comprising a means of remotely communicating with a device for processing and/or storing data of the computer type.

10. Device according to claim 1, wherein the device operates by autonomous power source of the battery type and/or from the mains.

11. Device according to claim 1, wherein said means for displaying, clearing are part of a case independent of the rigid frame for data acquisition.

* * * * *